Figure 1:
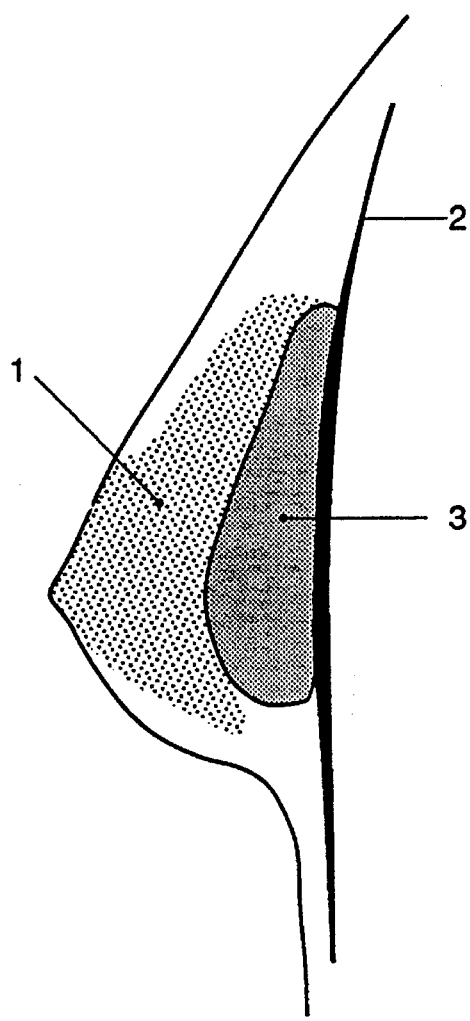

United States Patent
Kazem et al.

[11] Patent Number: 5,571,183
[45] Date of Patent: Nov. 5, 1996

[54] USE OF STARCH AND STARCH DERIVATIVES AS FILLER MATERIAL IN PROSTHESES

[75] Inventors: Farid Kazem, Hoorn; Ido P. Bleeker, Ten Boer; Henk J. Meijer, Groningen, all of Netherlands

[73] Assignee: Cooperatieve Verkoop - En Productievereniging Van Aardappelmeel en Derivaten Avebe B.A., Ja Veendam, Netherlands

[21] Appl. No.: 342,744

[22] Filed: Nov. 21, 1994

[30] Foreign Application Priority Data

Oct. 25, 1994 [EP] European Pat. Off. .............. 94203089

[51] Int. Cl.⁶ .................................................. A61F 2/02
[52] U.S. Cl. .................. 623/11; 623/8; 623/901; 623/66
[58] Field of Search ................ 623/7, 8, 11, 66, 623/901

[56] References Cited

U.S. PATENT DOCUMENTS

| | | |
|---|---|---|
| 4,731,081 | 3/1988 | Tiffany et al. . |
| 5,180,392 | 1/1993 | Skeie et al. ............... 623/11 |
| 5,219,360 | 6/1993 | Georgiade . |
| 5,376,117 | 12/1994 | Pinchuk et al. ............ 623/8 |

FOREIGN PATENT DOCUMENTS

| | | |
|---|---|---|
| 0054359A1 | 6/1982 | European Pat. Off. . |
| 0575035A2 | 12/1993 | European Pat. Off. . |
| 2568127 | 1/1986 | France . |
| WO87/04078 | 7/1987 | WIPO . |
| WO93/23089 | 11/1993 | WIPO . |

Primary Examiner—Robert A. H. Clarke
Attorney, Agent, or Firm—Hofmmann & Baron

[57] ABSTRACT

The present invention relates to a reconstructive prosthesis, for instance a breast prosthesis, comprising a container of a flexible, non-absorbable material, containing a filler material, wherein the filler material is an aqueous solution of a non-retrograding cross-linked starch or starch derivative. Preferably, the starch and/or starch derivative is cross-linked.

10 Claims, 1 Drawing Sheet

USE OF STARCH AND STARCH DERIVATIVES AS FILLER MATERIAL IN PROSTHESES

The present invention relates to the use of starch and starch derivatives in implants, more in particular in prostheses, especially reconstructive prostheses such as breast prostheses.

The type of prosthesis that forms the object of the present invention comprises a container or sac of a flexible, non-absorbable material filled with a fluid or gel filler material. It is conventional in this field of the art to use either saline solutions or silicone gels as filler material. Both materials have a number of disadvantages.

If saline solutions are used as a filler, a prosthesis is obtained with a rather unnatural feel and look. Moreover, such a prosthesis has a relatively low resistance to differences in pressure such as occur in an aeroplane or in deep-sea diving. Further, the prosthesis drains gradually within a period of about ten years. In this respect, it is noted that the loss of a saline aqueous solution does not have any adverse effect on the body; the salt will essentially be excreted by the kidneys.

The use of silicone gels in prostheses, and especially in reconstructive prostheses such as breast prostheses, involves a number of drawbacks. It is described in an article of Susan Katz Miller in New Scientist, 26 Jun. 1993, pages 22–24 and in the report of J.A.C. Linssen and H. Wolschrijn, titled "Siliconen Borstprotheses in Nederland" ("Silicone Breast Prostheses in the Netherlands"); Ed. Wetenschapswinkel Geneesmiddelen Utrecht (November 1993) that there are at least indications that the human or animal body responds to silicone gels when unintendedly released in the body. More in particular, it seems that silicone stimulates the immune system to produce antibodies and in some cases inflammatory responses. In such cases, it may be necessary to surgically remove the released silicone material and the infections. Further, the leakage of silicone filler material has been associated with other diseases and ailments, such as rheumatism, eye-trouble, and scleroderma.

More recently, the use of povidone (poly(N-vinyl-2-pyrrolidone) in breast prostheses is described. A prosthesis filled with povidone does not have a natural feel and look, although the feel and look are improved as compared with prostheses filled with saline solutions. In this light, it is additionally noted that povidone gives a dark blue colour to the prosthesis, which is adverse for the look of the implanted prosthesis. However, the most important disadvantage is the fact that povidone gives rise to immune reactions when it is released in the body. More in particular, povidone will bind to plasma proteins and interfere with thyroid gland functions.

It is the object of the present invention to provide a new filler material that overcomes the problems associated with the prior art filler materials.

The afore-mentioned problems are solved by using a solution, in particular an aqueous solution, of starch or a starch derivative as the filler material.

In one aspect, the present invention relates to a prosthesis for use in reconstructive surgery, for instance to a breast prosthesis, comprising a container of a flexible, non-absorbable material, containing a filler material, wherein the filler material is an aqueous solution of a non-retrograding starch or starch derivative.

Figure 2:
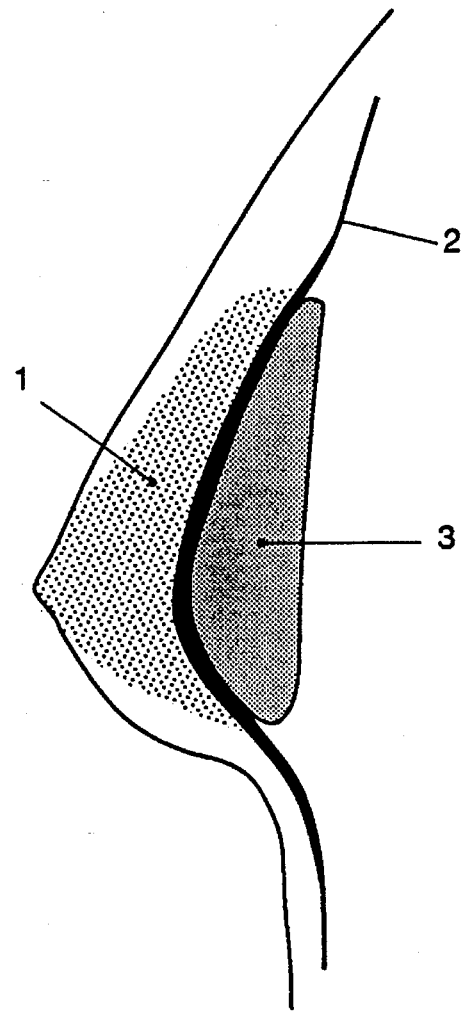

The in vivo placement of the breast implant prosthesis of the present invention into a host is shown as a side sectional view in FIGS. 1 and 2. FIG. 1 illustrates the subcutaneous placement of the breast implant (3) in the breast tissue of the host (1) anterior to the chest wall muscle (2). FIG. 2 illustrates the submuscular placement of the breast implant (3) in the breast tissue of the host (1) posterior to the chest wall muscle (2).

It is additionally noted that in U.S. Pat. No. 4,731,081 a flexible sac-type breast prosthesis is described, wherein a separate lubricating material is added to the filler material or inflating liquid in the sac. This lubricating material solves the problem which has been known as "fold flaw". One of the lubricating materials which may be added to the inflating liquid, which is generally a saline solution, in the sac-type prosthesis is hydroxyethyl starch.

Another prior art document where the use of starch, carbohydrates and amylose in breast prostheses is described is European patent application 0 054 359. However, this document does not teach the use of these materials as a filler material in a flexible sac, but in a biologically absorbable material surrounding the flexible sac. The function of this absorbable material is to effect capsule formation at a selected and controlled distance from the sac without giving rise to contractive pressure thereon after surgical implantation. It is possible to use this embodiment as a special embodiment of the present invention.

In a preferred embodiment, the prosthesis according to the invention comprises an aqueous solution of a cross-linked starch or starch derivative as the filler material. A suitable filler material is an aqueous solution comprising a cross-linked starch or starch derivative having a cross-linking degree of 0.01–0.5 percent. The cross-linking can be effected using well-known techniques, e.g. using epichlorohydrin, sodium trimetaphosphate or phosphoroxy chloride, while the cross-linking degree can be determined by all methods known to the man skilled in the art.

A breast prosthesis in accordance with the present invention has a natural look and feel when the starch or starch derivative solution has a Brookfield viscosity of between 500 mPa.s (Brookfield type RVT, spindle 5, 50 r.p.m.) and 50,000 mPa.s (type RVT, spindle 6, 20 r.p.m.) at a temperature of 25° C. Due to the relatively high molecular weight of starch or starch derivatives, these compounds will not drain from the flexible sac as compared with the known saline solutions.

Normally, the prostheses within the scope of the present invention comprise a solution containing about 5 to about 25 wt. % starch and/or starch derivatives. For the starches having a relatively low cross-linking degree, a 5%'s solution fits a required viscosity behaviour. In the case of higher cross-linking degree, concentrations of up to 25% are necessary to provide enough viscosity.

A very preferred breast prosthesis comprises 8% by weight of a starch derivative in an aqueous solution, which solution has a Brookfield viscosity of about 19,000 mPa.s (20 r.p.m.) and about 12,000 mPa.s (50 r.p.m.), measured at a temperature of 25° C.

Although any suitable solvent for starches and starch derivatives may be used if they do not adversely affect the body, the solvent used in combination with the starch or starch derivative is preferably water.

The prosthesis of the invention comprises a container or sac of a flexible, non-absorbable material. Suitable materials are different kinds of polymers, including natural rubber, polybutadiene, cellulose acetate, cellulose acetate butyrate, cellulose nitrate, cross-linked polyvinyl alcohol, polyurethane, nylon, polyvinyl acetate, polyvinyl butyrate, ethylene vinyl acetate copolymers, polyethylene, polypropylene etc. Preferably, the container is made of a silicone rubber material.

According to the invention, a non-retrograding starch or starch derivative is used. The term "starch" here refers to native starch and starch derivatives. The starch used may be of various origin, such as potato starch, amylopectin potato starch, corn starch, wheat starch, tapioca starch obtained by chemical, enzymatic and/or physical modification of native starch may also be used. The term "starch" as used herein also comprises such modified starch products.

The non-retrograding starch or starch derivative is suitably a potato starch or derivative thereof. In a preferred embodiment these starches are stabilized by monofunctional modification. In order to guarantee that the starches will degrade in the body if the prosthesis ruptures or leaks so that the filler material is released, the degree of substitution is within the range between 0.2 and 1.0, More in particular, the degree of substitution can be adjusted in such a way that the starch product can be derivatized in a suspension method while avoiding swelling of the product. A higher degree of substitution has the advantage that the solutions obtained are less sensitive to enzymatic degradation. However, the biodegradability also decreases with a higher degree of substitution, whereas the risk of provoking tissue reactions or other undesired side-reactions in the body increases.

Examples of starch derivatives that can be used in the present invention are starch ethers, preferably hydroxyalkyl starches, wherein the alkyl groups of the hydroxyalkyl substituents comprise 1–4 carbon atoms. Other suitable starch derivatives are starch esters, such as starch acetate, starch formate, starch propionate and starch butyrate.

The above-mentioned starch derivatives may be prepared by methods known to those skilled in the art. These methods are, e.g., described in the handbook "Modified Starches: Properties and Uses", Editor O. B. Wurzburg, M.S. Consultant National Starch and Chemical Corp. Bridgewater, N.J. (1986) CRC Press, Inc. Boca Raton, Fla. U.S.A.

Preferably, the starch-containing filler material solution is obtained by using a method in which potato starch is cross-linked and hydroxyethylated in an alkaline suspension. After neutralization of the reaction mixture, salts and other undesired products are washed out with a large amount of water. The derivatized starch is subsequently dried. In this way a very pure product is obtained, which can be made cold-water soluble by drum drying, extrusion of other known methods. Another possibility to obtain a solution comprises heating a suspension of the hydroxyethylated, cross-linked potato starch in water.

However, it is not necessary to use suspension methods to obtain suitable starch derivatives. Other methods that may comprise a purification step using dialysis, reprecipitation or washing with an alcohol-water mixture, can be used but are normally more expensive.

The use of a starch-based material as a filler material has a number of advantages. One of the most important advantages is the fact that this material is degradable, once it is accidentally released from the prosthesis envelope. The degradation products are low molecular products, which may be useful in the body or which can easily be excreted by the kidneys. The starches do not cause undesired tissue reactions.

Experiments carried out by the inventors showed that aqueous solutions of optimally cross-linked starch derivatives are the most suitable filler materials because of their rheological characteristics. The most preferred filler material is a hydroxyalkylated, preferably hydroxyethylated, cross-linked potato starch. This material is preferred for a number of reasons. First of all, this product is derived from potato starch. Potato starch is a product which by nature does not contain many impurities and is therefore relatively clean as compared with other starches. Cross-linking imparts such a visco-elastic character to this potato starch derivative that an excellent imitation of soft breast tissue is obtained. Further, hydroxyethyl starch is a product which has already been used in medical applications, e.g., as a blood plasma replacing agent. This will facilitate the registration procedure for the application of this material in prostheses. Moreover, it is known that hydroxyethylated starch is compatible with the body; it is degraded without problems and does not cause tissue reactions.

Dependent on the purpose of the prosthesis in reconstructive surgery, starch or starch derivatives are used in different amounts in an aqueous solution. Suitable prostheses can be made by the person skilled in the art without any difficulty. Normal amounts of the starch or starch derivatives to be used are 5–25 wt. %, based on the total of the solution, while the starch used is cross-linked with a cross-linking degree of 0.01–0.5%.

Finally, the invention relates to the use of starch and starch derivatives in a prosthesis comprising a flexible, non-absorbable sac, as structure-providing filling material.

The prosthesis of the present invention can be prepared using the same methods as are known to the skilled man for the preparation of prostheses filled with saline aqueous solutions or silicone gels. Before filling a sac of a flexible, non-absorbable material, the filling material preferably is sterilized, although it is also possible to sterilize the sac and filler material together. This sterilization may be carried out using well-known techniques, such as heating in water, or by treating the solution in an autoclave at 121° C. for 20 minutes.

The invention will be described in further detail with reference to the following examples.

EXAMPLE 1

Preparation of the filler material per se

A potato starch product (Potato starch AVEBE Foodgrade®) was cross-linked in suspension using epichlorohydrin, and hydroxyethylated using well-known techniques such as those described in the above-mentioned Handbook of Wurzburg. Subsequently, the modified starch suspension was washed with water to remove any undesired low molecular byproducts including salts. After this washing step, the product was drum dried.

In this way, a cross-linked, hydroxyethylated potato starch was obtained having a MS (HE) of 0.47 mol/mol, and a DS (HE) of 0.41 mol/mol. The Brookfield viscosity (type RVT, spindle 6, 25° C.) of a 8 percent by weight solution in demineralized water is 19,000 mPa.s (20 r.p.m.) and 12,000 mPa.s (50 r.p.m.).

In order to determine the degree of degradability of the derivatives in comparison with the potato starch starting material, the reductive power (DE; dextrin equivalent) was measured in an aqueous solution after a four hour reaction with pancreatin at 37° C., pH 7.1. The DE of potato starch was 43, while the DE of the derivative was only 9.9. This means that the derivative is considerably more difficult to degrade than dissolved potato starch.

EXAMPLE 2

The preparation of a breast prosthesis

An aqueous solution comprising 8 wt. % of the starch derivative prepared in Example 1 was heated in order to homogenize the solution.

The heated solution is introduced into a silicone container (INAMED) using a syringe. After filling the container, air bubbles were removed from the prosthesis obtained. Subsequently, the prosthesis was sealed with silicone glue (Silastic® Medical Adhesive, Silicone type A, Dow Corning). The sealed prosthesis was dried for 24 hours.

Before implantation, the prosthesis as a whole is sterilized. For that purpose, a 5-litre autoclave is filled with 300 ml water. The prosthesis is placed in a clean beaker in the autoclave. The autoclave is closed, while the valve remains open. The autoclave is heated on a heating plate until steam has escaped for 5 minutes through the valve. After closing the valve, the autoclave is heated at 121° C. for 20 minutes. Finally, the closed autoclave is allowed to cool to 80° C., whereafter the prosthesis is sterilely packed.

EXAMPLE 3

Comparison of different starches to be used as filler material

A number of drum dried cross-linked hydroxyalkylated starches were prepared as in Example 1. These products are described in Table 1:

TABLE 1

| Derivative | visc.@ | MS (HP/HE)* | Method of cross-linking |
| --- | --- | --- | --- |
| hydroxypropyl | 350 | 0.15 | 0.004 wt. % $POCl_3$ |
| hydroxypropyl | 7700 | 0.15 | 0.016 wt. % $POCl_3$ |
| hydroxypropyl | 200 | 0.15 | 0.093 wt. % $POCl_3$ |
| hydroxyethyl | 8300 | 0.18 | 0.010 wt. % ECH# |
| hydroxyethyl | 7700 | 0.17 | 0.025 wt. % ECH |
| hydroxyethyl | 310 | 0.18 | 0.050 wt. % ECH |
| hydroxyethyl | 10 | 0.18 | 0.100 wt. % ECH |

*hydroxypropyl or hydroxyethyl; molar substitution
epichlorohydrin
@Brookfield viscosity in mPa.s, T = 20° C., type LVT; 5 wt. % solution heated to a temperature of 90° C. while stirring during 10 minutes, followed by shearing using a Ultra Turrax (1000 r.p.m.; 2 min.).

The hydroxypropyl derivatives having a low degree of substitution were tested in a concentration of 10 wt. % in an aqueous solution. Following the procedure of Example 2, prostheses were prepared, except that the sterilization of the prostheses was effected by γ-radiation. The hydroxyethyl derivatives were heated in a water bath of 95° C. in aqueous solutions containing 6, 8 and 10 wt. % starch. After cooling the various solutions were evaluated on viscosity. It was noted that the viscosity of the solutions over a period of 1 week is not stable due to enzymatic degradation. The conclusion is that derivatives with a higher DS are more suitable.

The hydroxyethylated starch containing prosthesis that was irradiated with γ-rays was better in natural feel and look than the hydroxypropylated starch prosthesis. However, in both cases γ-irradiation led to degradation of the starch derivative and thereby to a decrease in viscosity. It is concluded that sterilization using γ-rays is less suitable for these types of prostheses.

The other three hydroxyethyl starch derivatives were evaluated on viscosity. The derivative cross-linked by using 0.05% ECH had the best viscosity characteristics for use in a breast prosthesis. Sterilization of prostheses filled with these starch solutions using an autoclave (121° C./15 min) did not have an adverse effect on the viscosity.

EXAMPLE 4

In vivo test results of the implantation of the prosthesis of the invention

In order to determine the reaction of normal tissues to the implantation of a breast prosthesis consisting of a conventional silicone sac filled with a solution of a starch derivative and the reaction between normal tissues and the filler material per se, the following animal tests were carried out.

The tests were performed on two sheep and ten rats.

More in particular, the tissue reaction was demonstrated using known histological techniques. In both sheep, four conventional silicone sacs comprising the hydroxyethyl starch solution of Example 1 (MS(HE)=0.47 mol/mol, DS(HE)=0.41 mol/mol) were implanted. Three of these test prostheses were placed subcutaneously, the fourth one submuscularly. The submuscular sac and one of the subcutaneous sacs were intact. In order to monitor the tissue reaction to the prosthesis filler material, one of the subcutaneous sacs was leaking when implanted. The third subcutaneous sac was punctured five weeks after implantation in order to study the effects of leakage after the formation of a capsule around the sac by the body. Thirteen weeks after implantation, both sheep were sacrificed for the purpose of histological examination.

At the dorsal side of each rat, an area of 3×3 cm was marked off at the height of the shoulders. In this area, 2 cc of prosthesis filler material was injected. The tissue reaction was monitored both objectively and histologically over a period of 4 weeks. For the histological examinations, each week one rat was sacrificed.

In both sheep, objectively normally formed capsules were found around all implanted prostheses. With none of the four intact prostheses was prosthesis filler material found outside or within the capsule formed around the silicone sac. Also with the prostheses punctured before implantation, intact capsules were formed and objectively unaltered filler material was found outside the silicone sac. No filler material was found outside the capsule, while there were no indications for inflammatory reactions. Even in the area of the silicone sac which was punctured after five weeks, no infections were found, while all filler material remained within the capsule formed around the silicone sac.

In the rats which were injected with the prosthesis filler material, no tissue reactions could objectively be demonstrated neither within nor outside the marked off areas. The injected filler material objectively disappeared after one day. After one week, it could no longer be detected in the tissues surrounding the injection place. In the histological preparations, microscopic examinations revealed that a process took place which is indicative of degradation of the prosthesis filler material.

We claim:

1. A reconstructive prosthesis comprising:
   a container made from a flexible, non-absorbable material; and
   a filler material contained within said container, wherein said filler material is an aqueous solution of a non-retrograding cross-linked starch or starch derivative.

2. The prosthesis according to claim 1, wherein said non-retrograding starch is cross-linked potato starch.

3. The prosthesis according to claim 1, wherein said cross-linked starch is a cross-linked starch having a cross-linking degree of 0.01–0.5 percent.

4. The prosthesis according to claim 1, wherein said cross-linked starch is a hydroxyalkylated cross-linked starch.

5. The prosthesis according to claim 4, wherein said hydroxyalkylated cross-linked starch is a hydroxyethylated cross-linked starch.

6. The prosthesis according to claim 5, wherein said hydroxyethylated cross-linked starch is hydroxyethylated cross-linked potato starch.

7. The prosthesis according to claim 1, wherein said aqueous solution has a Brookfield viscosity between 500 mPa.s (type RVT, spindle 5, 50 r.p.m.) and 50,000 mPa.s (type RVT, spindle 6, 20 r.p.m.), at a temperature of 25° C.

8. The prosthesis according to claim 1, wherein said flexible, non-absorbable material of said container is selected from the group consisting of natural rubber, polybutadiene, cellulose acetate, cellulose acetate butyrate, cellulose nitrate, cross-linked polyvinyl alcohol, polyurethane, nylon, polyvinyl acetate, polyvinyl butyrate, ethylene vinyl acetate copolymers, polyethylene and polypropylene.

9. The prosthesis according to claim 1, wherein said flexible, non-absorbable material of said container is a silicone material.

10. A method of making a reconstructive prosthesis, which comprises:

filling a container made from a flexible, non-absorbable material with a filler material comprising an aqueous solution of a non-retrograding cross-linked starch or starch derivative.

* * * * *